(12) United States Patent
Wei et al.

(10) Patent No.: US 11,629,362 B2
(45) Date of Patent: Apr. 18, 2023

(54) REPLICATIVE ONCOLYTIC ADENOVIRUS FOR REGULATING LIPID METABOLISM AND USE THEREOF

(71) Applicant: NANJING NOVEL BIOTECHNOLOGY CO., LTD., Nanjing (CN)

(72) Inventors: Jiwu Wei, Nanjing (CN); Jie Dong, Nanjing (CN); Tiancheng Xu, Nanjing (CN); Lingkai Kong, Nanjing (CN); Guanqun Wo, Nanjing (CN)

(73) Assignee: Nanjing Novel Biotechnology Co., Ltd, Nanjing (CN)

( * ) Notice: Subject to any disclaimer, the term of this patent is extended or adjusted under 35 U.S.C. 154(b) by 0 days.

(21) Appl. No.: 17/676,152

(22) Filed: Feb. 19, 2022

(65) Prior Publication Data

US 2022/0195463 A1    Jun. 23, 2022

Related U.S. Application Data

(63) Continuation-in-part of application No. PCT/CN2020/078360, filed on Mar. 9, 2020.

(30) Foreign Application Priority Data

Aug. 19, 2019   (CN) .......................... 201910766671.1

(51) Int. Cl.
*A61K 35/761* (2015.01)
*A61K 48/00* (2006.01)
*A61P 35/00* (2006.01)
*C12N 15/86* (2006.01)

(52) U.S. Cl.
CPC ............ *C12N 15/86* (2013.01); *A61K 35/761* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 2007/0031379 A1 | 2/2007 | Lee et al. | |
| 2013/0323206 A1 | 12/2013 | Yun et al. | |
| 2014/0140959 A1* | 5/2014 | Szalay | A61K 41/0052 435/235.1 |
| 2016/0040185 A1* | 2/2016 | Hwang | C12N 15/85 435/325 |
| 2018/0185515 A1 | 7/2018 | Hicklin et al. | |
| 2018/0201664 A1* | 7/2018 | Hayden-Ledbetter | C12Y 301/01002 |

FOREIGN PATENT DOCUMENTS

| | | |
|---|---|---|
| CN | 1884556 A | 12/2006 |
| KR | 1020090093706 A | 9/2009 |
| WO | 199822606 A1 | 5/1998 |
| WO | 2002067861 A2 | 9/2002 |
| WO | 2005086922 A2 | 9/2005 |

OTHER PUBLICATIONS

Stoffel et al, Synthesis in vitvo and Translocation of Apolipoprotein A1 across Microsomal Vesicles, Eur. J Biochem. 120. 519-523 (1981).*
Seo. J et al. "A proteoliposome containing apolipoprotein A-I mutant (VI56K) enhances rapid 1-15 tumor regression activity of human origin oncolytic adenovirus in tumor-bearing zebrafish and mice", Molecules and Cells, vol. 34 No. 2 Jul. 30, 2012 (Jul. 30, 2012)., pp. 143-147.
Wang. Qian et al. (non-official translation: Research on the Construction of Recombinant Oncolytic Adenovirus rAd-CMV-EIA and its Radiosensitization to Human Nasopharyngeal Carcinoma Cells), Journal of Modern Oncology, vol. 25. No. 16. Jul. 2, 2017 (Jul. 2, 2017). pp. 2545-2551, abstract only.
Kim et al, "Human apolipoprotein(a) kringle V inhibits angiogenesis in vitro and in vivo by interfering with the activation of focal adhesion kinases," Biochemical and Biophysical Research Comm, 313 534-40 (2004).
Geest Bart De et al: "Sustained Expression of Human Apolipoprotein A-I after Adenoviral Gene Transfer in C57BL/6 Mice: Role of Apolipoprotein A-I Promoter, Apolipoprotein A-I Introns, and Human Apolipoprotein E Enhancer", Human Gene Therapy, vol. 11, No. 1, Jan. 1, 2000, pp. 101-112.
Z-B Hu et al: "A simplified system for generating oncolytic adenovirus vector carrying one or two transgenes", Cancer Gene Therapy, vol. 15, No. 3, Dec. 21, 2007, pp. 173-182.
Signe Borgquist et al: "Apolipoproteins, lipids and risk of cancer", International Journal of Cancer, John Wiley & Sons, Inc, US, vol. 138, No. 11, Feb. 8, 2016, pp. 2648-2656.
Georgila, Konstantina et al., "Apolipoprotein A-I (ApoA-1), Immunity, Inflammation and Cancer," Cancers, vol. 11, No. 1097, pp. 1-25, Published: Aug. 1, 2019.
Su, Feng et al., "Apolipoprotein A-I (apoA-1) and apoA-1 mimetic peptides inhibit tumor development in a mouse model of ovarian cancer," PNAS, 2010, vol. 107, No. 46, pp. 19997-20002.

* cited by examiner

*Primary Examiner* — Maria Marvich
(74) *Attorney, Agent, or Firm* — Perkins Coie LLP

(57) ABSTRACT

Provided are embodiments of replicative oncolytic adenovirus AD5 ApoA1 for inhibiting tumor growth and metastasis and use thereof in preparation of anti-tumor drugs. The virus can rapidly replicate in tumor cells and exert an oncolytic effect. Tumor cells infected with the virus can highly express apolipoprotein ApoA1 which can be secreted extracellularly in large quantities, significantly inhibit the invasion and metastasis of tumor cells, inhibit tumor-promoting inflammation pathways, and significantly reduce a IDO-1 which is a key molecule that leads to tumor immune escape. The virus can significantly inhibit tumor growth, inhibit tumor invasion, delay progression of cachexia and prolong the survival time of tumor-bearing mice in mice with liver cancer, breast cancer, colon cancer, or lung cancer.

7 Claims, 14 Drawing Sheets

Specification includes a Sequence Listing.

FIG 2(A)
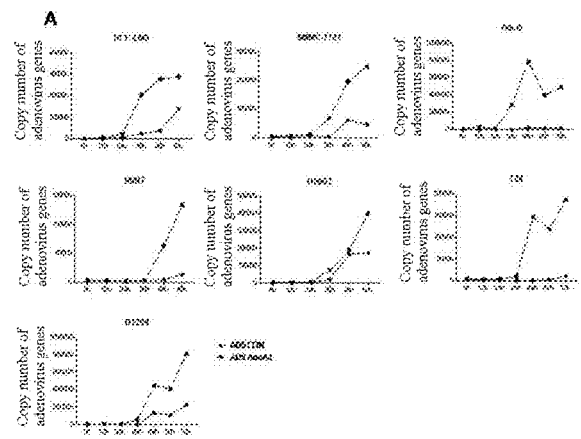
FIG 2(B)
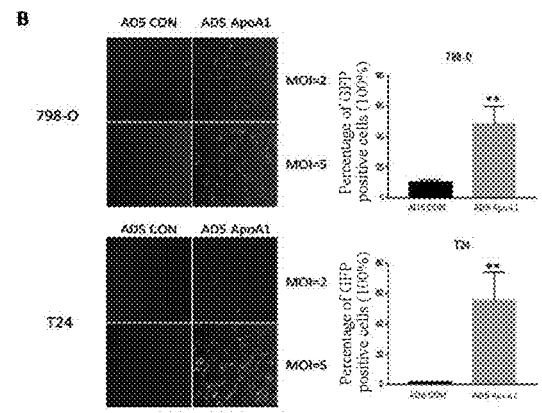
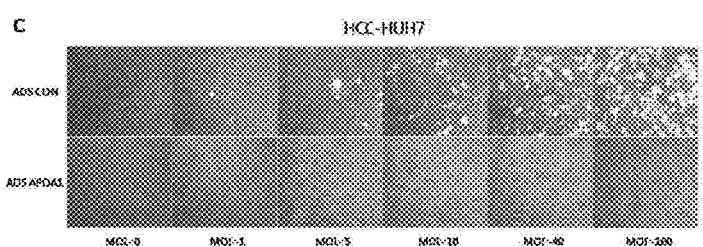
FIG 2(C)
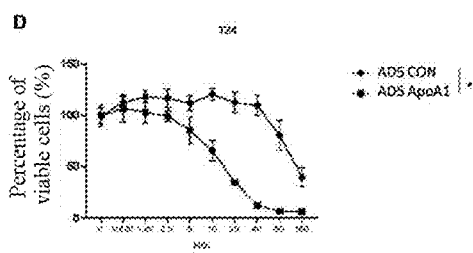
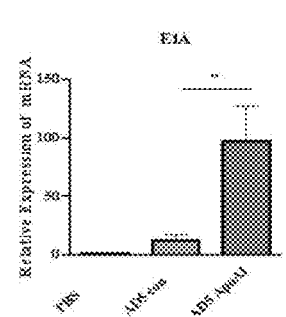
FIG 2(D)
FIG 2(E)

FIG 3(A)
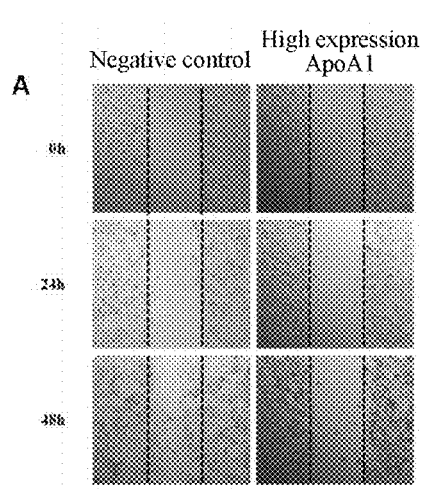
FIG 3(C)
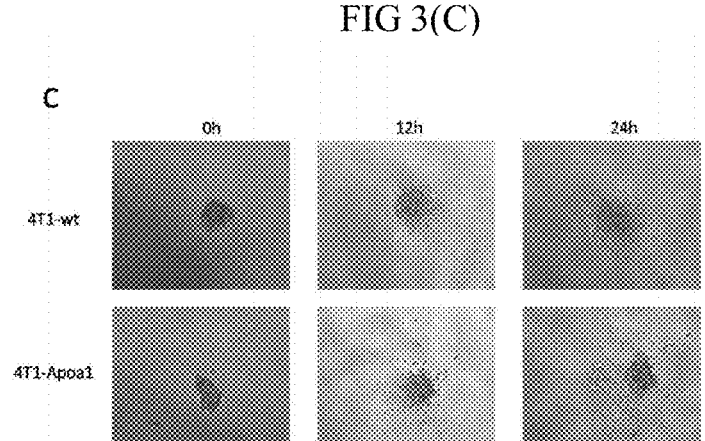
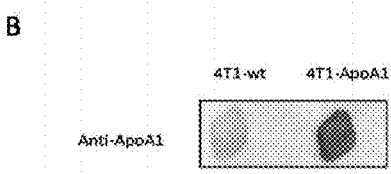
FIG 3(B)
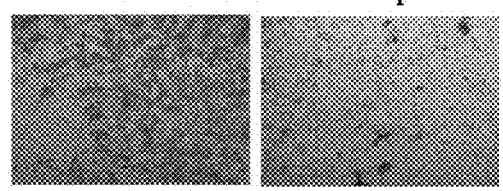
FIG 3(D)

FIG 4(A)
FIG 4(B)
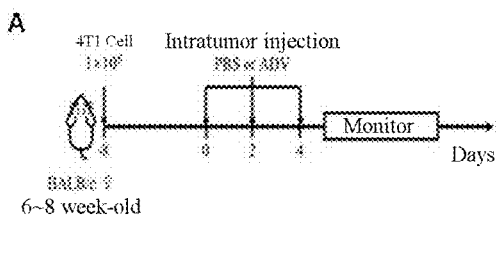
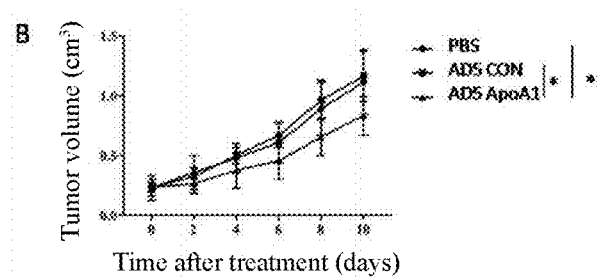
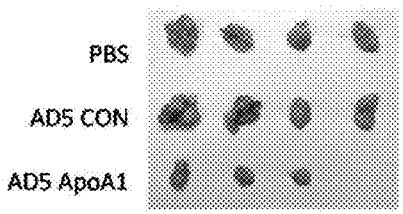
FIG 4(C)
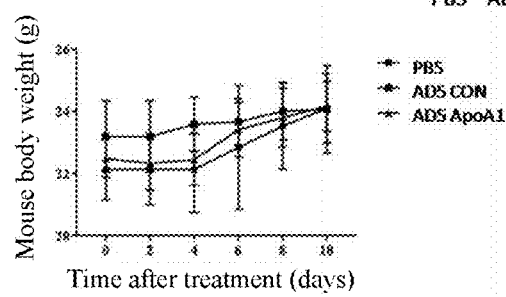
FIG 4(D)

FIG 5(A)
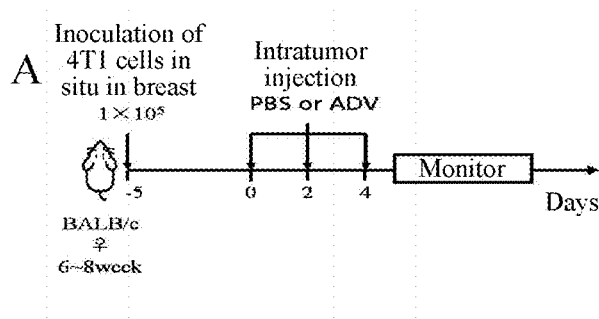
FIG 5(B)
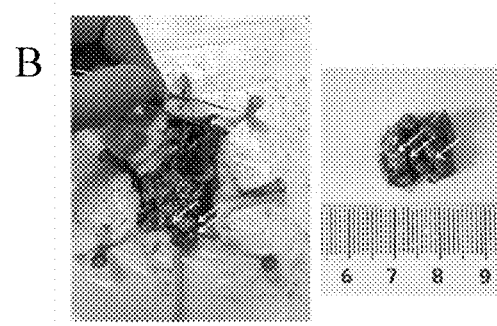
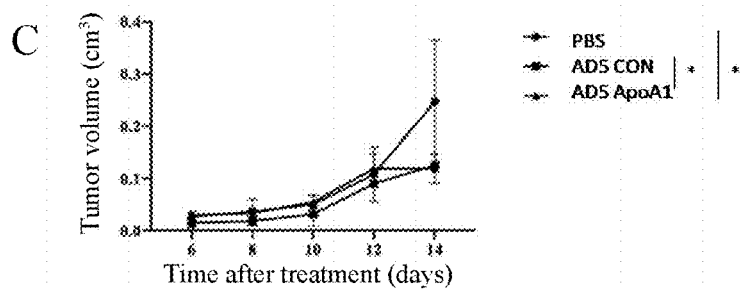
FIG 5(C)
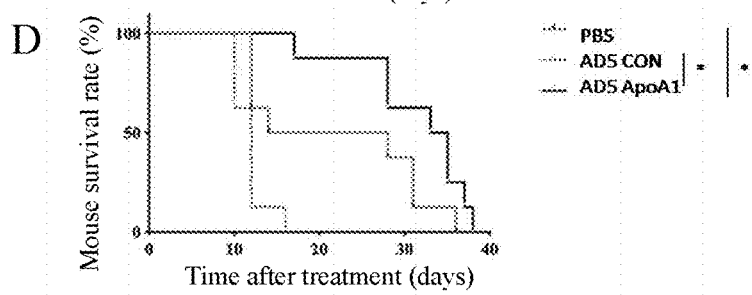
FIG 5(D)

FIG 8(A)
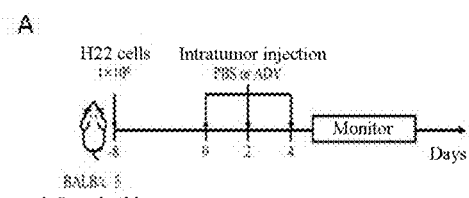
FIG 8(B)
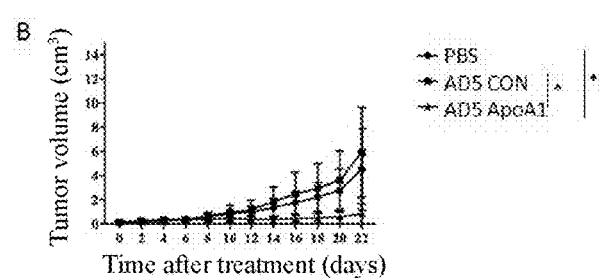
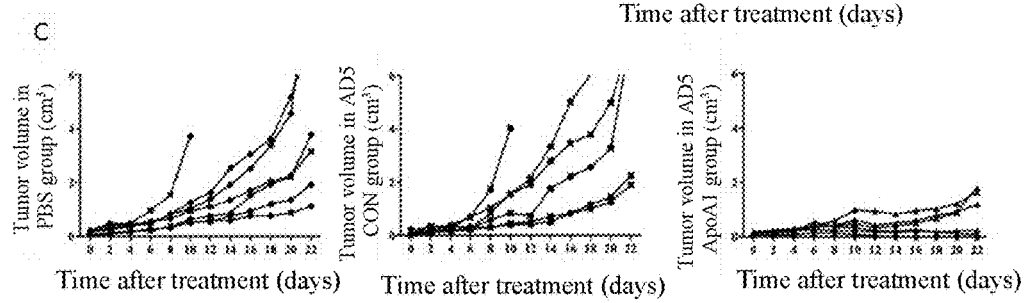
FIG 8(C)
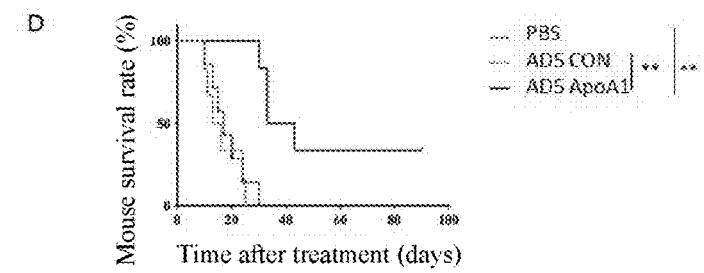
FIG 8(D)

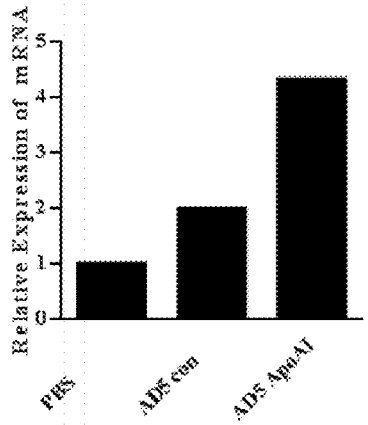
FIG. 11
FIG. 12(A)
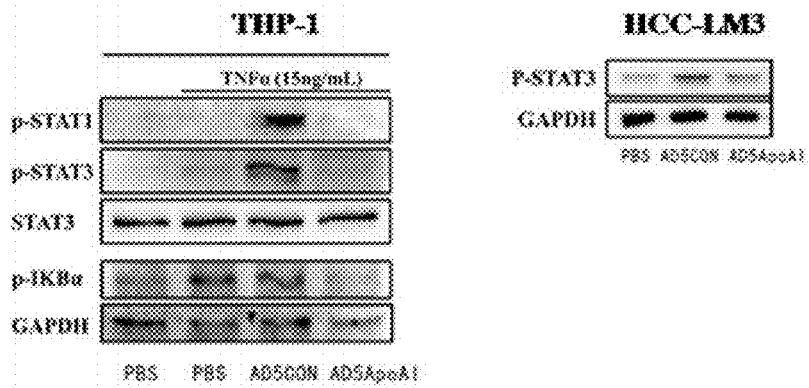
FIG. 12(B)
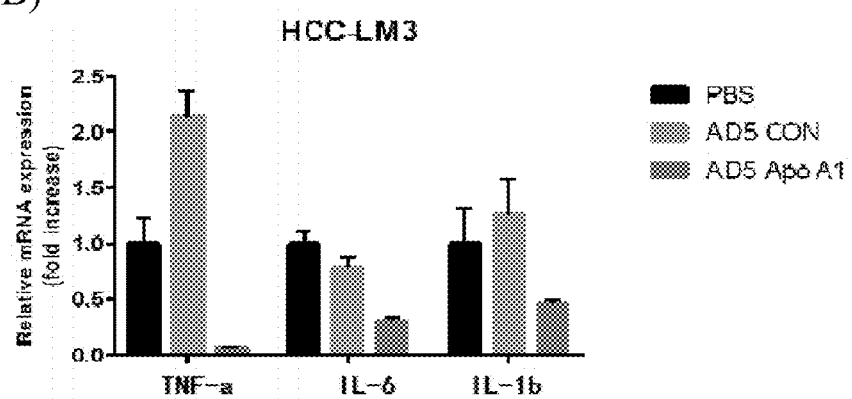

REPLICATIVE ONCOLYTIC ADENOVIRUS FOR REGULATING LIPID METABOLISM AND USE THEREOF

CROSS REFERENCE TO RELATED APPLICATIONS

This application is a continuation in part of International Application No. PCT/CN2020/078360, filed Mar. 9, 2020, which claims the benefit of Chinese Patent Application No. 201910766671.1, filed Aug. 19, 2019, both of which are incorporated by reference herein in their entirety.

SEQUENCE LISTING

This application contains a Sequence Listing, which was submitted in ASCII format via EFS-Web and is hereby incorporated by reference in its entirety. The ASCII copy, created on Feb. 19, 2022, is named Nanjing Sequence Listing 146478-8001.US00_ST25.txt and is 5 KB in size.

TECHNICAL FIELD

The present invention relates to the field of tumor biotherapy, and relates to a replicative oncolytic adenovirus for effectively inhibiting tumor growth, invasion and metastasis, and use thereof.

BACKGROUND

There are about 4 million new cancer patients in China every year, and nearly 3 million people die from cancer every year. Traditional surgery, radiotherapy, chemotherapy and other solutions have inhibited tumor progression to a certain extent, but invasion, metastasis and recurrence of tumors are difficult to control.

In recent years, tumor biotherapy has become an indispensable part. An oncolytic virus itself can replicate in tumor cells and play an oncolytic effect. At the same time, it can activate immune cells, cause immune cell infiltration in a tumor area, and induce an anti-tumor immune response. In addition, an oncolytic virus can carry foreign genes, express foreign proteins in a tumor area, and directly exert an anti-tumor effect of a protein drug. In 2015, the first oncolytic virus drug (T-Vec, Amgen) was approved for marketing by the FDA. The recombinant herpes simplex virus-1 can express GM-CSF to activate DC to exert anti-tumor activity. Development of drugs of oncolytic viruses in the prior art mainly involves constructing recombinant expression vectors to release immune activating factors or immune checkpoint antibodies by the viruses to activate a patient's immune function in order to exert anti-tumor effects, for example, a recombinant oncolytic adenovirus carrying a human cell-penetrating peptide p53 and a GM-CSF gene (CN201310460980), and a Newcastle disease oncolytic virus expressing a PD-L1 single-stranded antibody (CN201811560794). However, currently tumor metastasis cannot be effectively controlled by the prior art.

Apolipoprotein ApoA1 is the most abundant component in the ApoA family. It is synthesized in livers and small intestines and is a single polypeptide composed of 243 amino acid residues. ApoA1 is an activator of lecithin cholesterol acyltransferase, mainly present in high-density lipoprotein (HDL), and is a main apolipoprotein of HDL. A main function of ApoA1 is to mediate reverse transport of cholesterol, that is, transport cholesterol from peripheral tissue to liver. ApoA1 binds to its specific receptor adenosine triphosphate binding cassette transporter A1 (ABCA1) on cell surface to take up cellular free cholesterol and phospholipids to generate new HDL. Free cholesterol in HDL particles is converted to cholesterol lipids by lecithin cholesterol acyltransferase (LCAT), which are then transported to the liver for metabolism. It has been reported that, a complex formed by coupling proteoliposomes (PL) carrying wild-type (WT) or mutant (V156V) ApoA1 with an oncolytic adenovirus can effectively improve the anti-tumor activity of the oncolytic virus on Hep3B cells (Mol Cells. 2012; 34: 143-148). However, this technical solution does not provide similar technical effects on tumor invasion, metastasis or recurrence. In addition, the technical solution reported exerts an effect by firstly, constructing PL from dimyristoylphosphatidylcholine (DMPC), free cholesterol (FC) and ApoA1 in a composition ratio of 200:9:1 in vitro, and then forming a complex with an oncolytic adenovirus. This method not only involves complicated preparation process, but also is effective for a relatively short period of time.

Therefore, there is still a lack of replicative oncolytic virus vectors and oncolytic viruses capable of expressing genes related to lipid metabolism, which can effectively inhibit tumor growth and control metastasis and recurrence.

SUMMARY

The objective of the present invention is to provide a replicative oncolytic adenovirus for inhibiting tumor growth, invasion and metastasis, and use thereof.

To achieve the above objective, the present invention adopts the following technical solutions:

A replicative oncolytic adenovirus vector and recombinant oncolytic virus capable of secreting an apolipoprotein ApoA1. Specifically, an embodiment of a construction of the replicative oncolytic adenovirus vector includes: a laboratory grade tagged adenovirus vector and a pharmaceutical grade untagged adenovirus vector. The laboratory grade adenovirus replicative element E1A is controlled by a first constitutive promoter CMV. A GFP sequence is ligated upstream of the E1A, and an A2 linker sequence is ligated in between. A foreign target gene ApoA1 inserted into an E1 region is controlled by a second constitutive promoter CMV or EF1a promoter. ApoA1 has a signal peptide sequence at the 5' end, and a His tag sequence and a PA sequence at the 3' end.

This embodiment constructs a recombinant oncolytic adenovirus capable of replicating in tumor cells to kill tumor cells and inhibit tumor growth, and the recombinant oncolytic adenovirus can express and secrete ApoA1 protein, which is a transport protein involved in lipid metabolism. It was found that the replicative recombinant ApoA1-expressing oncolytic adenovirus can inhibit invasion and metastasis of tumor cells.

Thus, the following inventions are provided.

(1) One aspect of the present invention relates to construction of a replicative oncolytic adenovirus AD5-ApoA1 vector, which is operably inserted with or includes the following foreign genes:

An ApoA1 target gene sequence or a degenerate sequence thereof, with a nucleotide sequence such as SEQ ID NO:1, specifically, the 5' end of which includes a signal peptide recognition sequence;

wherein ApoA1 is located in an E1 region of an adenovirus, preferably an E1B region.

Vector construction of the replicative oncolytic adenovirus AD5-ApoA1 according to any embodiment of the present invention, the vector is operably inserted with or includes the following foreign genes:

Laboratory grade: A first promoter, a GFP sequence, a 2A linker sequence, an E1A early activation replication element, an insulator sequence, a second promoter, a target gene sequence or a degenerate sequence thereof, a His tag sequence, and a PA sequence which are ligated in sequence.

Specifically, the first promoter, the GFP sequence, the 2A linker sequence, and the E1A early activation replication element are in the same expression cassette.

The second promoter, the target gene sequence or the degenerate sequence thereof, the His tag sequence, and the PA sequence are in the same expression cassette; the promoter may be a constitutive promoter, an inducible promoter, or a specific promoter; preferably, the first promoter may be a constitutive promoter, an inducible promoter, or a specific promoter; and the second promoter may be also a constitutive promoter. The constitutive promoter is preferably CMV, SV40 or EF1a. More preferably, the constitutive promoter is a CMV promoter, and has a nucleic acid sequence as shown in SEQ ID NO:2.

Pharmaceutical grade: A first promoter, an E1A early activation replication element, an insulator sequence, a second promoter, a target gene sequence or a degenerate sequence thereof, and a PA sequence which are ligated in sequence.

An example of the protein amino acid sequence of the expressed ApoA1 gene is SEQ ID NO:3.

Vector construction of the replicative oncolytic adenovirus AD5 ApoA1 according to any embodiment of the present invention is characterized in that the oncolytic adenovirus includes subclasses A, B, C, D, E and F, preferably subclass C adenoviruses, and more preferably, a human adenovirus type 5 AD5.

(2) Another aspect of the present invention relates to a replicative oncolytic adenovirus, which comprises the recombinant oncolytic adenovirus vector according to any embodiment of the present invention, including an E1A replication element, and an ApoA1 independent expression cassette; and the specific recombinant oncolytic virus vector is obtained by recombination in 293T cells.

(3) A yet another aspect of the present invention relates to uses of any replicative oncolytic adenovirus vector or any replicative oncolytic adenovirus of the present invention in inhibiting tumor invasion and metastasis, alleviating tumor cachexia, inhibiting tumor inflammation, and anti-tumor immunotherapy drugs; and specifically, the cancer or tumor is liver cancer, breast cancer, lung cancer, colon cancer, stomach cancer, pancreatic cancer, cervical cancer, melanoma, prostate cancer, ovarian cancer, lymphoma, gallbladder cancer, esophageal cancer, renal cancer, nasopharyngeal cancer, laryngeal cancer, thyroid tumor, mediastinal tumor or glioma, preferably liver cancer, breast cancer, lung cancer, colon cancer, and bladder cancer.

Tumor invasion and metastasis are the underlying causes of death of cancer patients. At present, there is no anti-tumor drug capable of effectively controlling tumor invasion or metastasis, and there is no confirmed oncolytic virus drug capable of inhibiting tumor invasion or metastasis. The recombinant replicative oncolytic adenovirus AD5-ApoA1 described in the present invention is the first oncolytic virus confirmed to be capable of inhibiting invasion and metastasis of malignant tumors so far.

In addition, the chance of developing cachexia in advanced tumor is more than 60%, which is also a main contributing factor to the death of advanced cancer patients. The most significant symptom of cachexia is progressive emaciation (weight loss). There is no clinically effective drug or method to delay tumor cachexia. The recombinant replicative oncolytic adenovirus AD5-ApoA1 of the present invention has an unexpected effect of inhibiting progression of cachexia, and can effectively maintain the body weight of colon cancer mice and significantly extend the survival time.

The replicative oncolytic adenovirus can also effectively up-regulate a specific receptor ABCA1 of ApoA1 highly expressed by infected tumor cells, and can greatly enhance the cholesterol transport effect of AD5 ApoA1, resulting in an unexpected synergistic effect. Finally, AD5 ApoA1 can also effectively control a tumor-promoting inflammation pathway, inhibit a key enzyme IDO-1 which mediates tumor immune escape, and effectively restore a body's immune surveillance of tumors. In summary, the recombinant replicative oncolytic adenovirus AD5 ApoA1 of the present invention simultaneously has multiple anti-tumor effects: inhibiting tumor invasion and metastasis, delaying a cachexia progress of malignant tumors, up-regulating the specific receptor ABCA1 of ApoA1 highly expressed by infected tumor cells for synergistic anti-tumor effects, inhibiting IDO-1 and tumor-promoting inflammation, and restoring anti-tumor immune surveillance. The above effects cooperate with each other and produce excellent anti-tumor effects, so that the recombinant replicative oncolytic adenovirus can be used to prepare an anti-tumor drug.

Specifically, certain embodiments of the present invention provide:

1) A construction scheme for the replicative oncolytic adenovirus AD5 ApoA1. After AD5 ApoA1 infects cells, the cells can express and secrete an apolipoprotein ApoA1;

2) Compared with a control virus, the replicative AD5 ApoA1 has stronger replicative and oncolytic ability in tumor cells;

3) The apolipoprotein ApoA1 significantly inhibits invasion and metastasis of breast cancer cells;

4) In an animal experiment, the replicative AD5 ApoA1 significantly inhibits the growth of breast cancer subcutaneous tumors in mice;

5) In an animal experiment, the replicative AD5 ApoA1 significantly inhibits invasion and metastasis of breast cancer in situ in mice, and significantly extends the survival time of mice;

6) In an animal experiment, the replicative AD5 ApoA1 significantly inhibits the growth of lung cancer in mice;

7) In an animal experiment, the replicative AD5 ApoA1 significantly inhibits the growth of colon cancer in mice, and can significantly alleviate progression of cachexia in mice;

8) In an animal experiment, the replicative AD5 ApoA1 significantly inhibits the growth of liver cancer in mice and significantly extends the survival time of mice;

9) In a humanized mouse model, the replicative AD5 ApoA1 significantly inhibits the growth of liver cancer and significantly extends the survival time of mice;

10) In breast cancer cells, the replicative ApoA1 significantly inhibits a key protein K14 which promotes tumor invasion;

11) In cancer cells, the replicative AD5 ApoA1 significantly up-regulates the APOA1 specific receptor ABCA1 (enhancing the ability of APOA1 to transport cholesterol);

12) In macrophages and liver cancer cells, the apolipoprotein ApoA1 significantly inhibits activation of STAT3, a key molecule which promotes tumor inflammation; and 13) In macrophages and liver cancer cells, the apolipoprotein ApoA1 significantly reduces IDO-1, a key enzyme which inhibits anti-tumor immunity.

DETAILED DESCRIPTION OF THE INVENTION

The term "ApoA1" has a gene ID: 335 in NCBI. The gene encodes the apolipoprotein A-I, which is the main protein component of high-density lipoprotein (HDL) in plasma. A precursor protein encoded by the gene produces a mature protein via proteolysis, which promotes excretion of cholesterol from tissues to the liver, and is a cofactor of lecithin cholesterol acyltransferase (LCAT). LCAT is an enzyme responsible for formation of most plasma cholesteryl esters. The gene is closely related to another two apolipoprotein genes on chromosome 11. Defects in the gene are related to high-density lipoprotein deficiency, including Tangier disease, and systemic non-neural amyloidosis. Alternative splicing results in multiple transcript variants, at least one of which encodes a preprotein.

There are multiple transcripts of the ApoA1 gene, e.g., NM_000039.2/NP_000030.1 (cDNA sequence/protein sequence), NM_001318017.2/NP_001304946.1, NM_001318018.2NP_001304947.1 and NM_001318021.1NP_001304950.1.

The term "E1A:" E1 region genes of a virus can be further divided into E1A and E1B. E1A mainly includes two components, namely 289R (or 13S) and 243R (or 12S). After the adenovirus genome enters a cell nucleus, a cell transcription factor first binds to an enhancer upstream of the E1A region to express an E1A protein, the function of which is to regulate cell metabolism and make viral DNA easier to replicate in the cell. The E1A protein can also activate promoters of other early genes (E1B, E2A, E2B, E3 and E4), wherein E2B drives expression of precursor terminal protein (pTP), single-stranded DNA binding proteins (ssDBP), and DNA polymerase (DNA pol) that related to virus replication. Expression products of the three genes form into a complex, which interacts with at least three cellular proteins to initiate replication of the viral genome. In certain embodiments of the present invention, an independent CMV promoter is included before E1A. GFP and E1A are ligated by a 2A linker sequence.

Without being bound by theory, 2A itself, as the linker sequence, has only post-translational protein cleavage sites, and 2A peptide will remain in proteins before and after 2A. GFP is ligated with E1A by 2A to separate an early replication element from a GFP-tagged protein.

Without being bound by theory, more than 100 serotypes have been found in the selection of adenovirus serotypes, of which 52 serotypes are human adenoviruses that are divided into six subgroups (A, B, C, D, E and F). The human adenoviruses have different tropism to host cells, tumorigenicity and disease history. The type 2 and type 5 human adenoviruses commonly used in gene therapy belong to the C subgroup in serology, with 95% homology in DNA sequence. A process of adenovirus infection of cells starts from adhesion of a head region of an adenovirus fiber to a specific receptor on a cell surface. Because human adenovirus mainly shares a receptor with Coxsackie B virus, the receptor is called a coxsackie/adenovirus receptor (CAR). Low-level expression of CAR restricts a transduction efficiency of adenoviruses. However, since a C subgroup adenovirus vectors have been successfully put in clinical use, the safety of said vectors has been extensively tested in humans and is high. The recombinant adenovirus of the present invention can be replicated in tumor cells.

The drugs of certain embodiments of the present invention can be manufactured by methods well known in the art, such as conventional biologically active preparations, e.g., inactivated vaccines and vaccine viruses, etc. Preferably, the biological preparation is an attenuated live vaccine virus.

Uses of the drug of certain embodiments of the present invention includes three aspects: as preventive products, therapeutic products, and diagnostic products. Preferably, the use is as a therapeutic product. The therapy may be a single-drug therapy, adjuvant therapy or combination therapy.

Administration routes of the drug of certain embodiments of the present invention include but are not limited to oral, rectal, transmucosal, and enteral administration, or topical, transdermal, inhalation, parenteral, sublingual, intravaginal, intranasal, intraocular, intraperitoneal, intramuscular, subcutaneous, intravenous, and tumor in situ administration. Preferred administration routes are intravenous injection and tumor in situ administration.

BRIEF DESCRIPTION OF THE DRAWINGS

FIGS. 2(A)-2(E) show replication and oncolysis of the recombinant oncolytic adenovirus AD5 ApoA1 of an embodiment of the present invention. 2(A) Human liver cancer cell line HCC-LM3 and SMMC-7721, human renal clear cell cancer cell line 786-0, human liver cancer cell line HuH-7 and HepG2, human bladder cancer cell line T24, and human lung cancer cell line H1299 were infected with AD5 CON and AD5 ApoA1 at a MOI of 0.1, respectively, then cells were collected at the corresponding time points, the viral genomic DNA was extracted, and the copy number of AD5 was detected by Q-PCR. The P values were all less than 0.01. 2(B) Human renal clear cell cancer cell line 786-0 or human bladder cancer cell line T24 were infected with viruses at various MOIs, 24 h after infection, the number of virus-infected cells was detected by a fluorescence microscope or flow cytometry. Green fluorescent proteins represent viral infection. 2(C) Human liver cancer cell line HuH-7 was infected with the AD5 CON and AD5 ApoA1 viruses at various MOIs, 72 h after infection, the cell morphology was observed under a microscope. 2(D) Human bladder cancer cell line T24 was infected with the AD5 CON and AD5 ApoA1 viruses at various MOIs, 72 h after infection, the cell viability was detected by CCK8. 2(E) Balb/c mice were inoculated with 4T1 tumor cells, after the tumor formed, $2.5 \times 10^8$ pfu AD5 CON or AD5 ApoA1 virus was injected intratumorally. 48 h later, the expression of viral E1A gene was quantified by qPCR to determine the viral copies. *, $p<0.05$, **, $p<0.01$, and the data was obtained by three independent repeated experiments.

FIGS. 3(A)-3(D) show that ApoA1 inhibited metastasis and invasion of breast cancer cells 4T1 in vitro. 3(A) Mouse breast cancer cells 4T1 were transiently transfected with a non-replicative adenovirus expressing ApoA1 or a negative control, 72 h later, the migration of cells to a scratch was observed under a microscope. 3(B) A stable transfected cell line of 4T1 stably expressing ApoA1 was constructed. After wild-type 4T1 cells (4T1-wt) and 4T1 cells with high ApoA1 expression (4T1-ApoA1) were cultured for 24 h, supernatants were collected, and the secretion level of ApoA1 was detected by Western blot. 3(C) 4T1-wt or 4T1-ApoA1 cells were subjected to hanging drop culture to obtain cell clones, and then the cell clones were inoculated into a 96-well cell culture plate coated with type I collagen. The cells were monitored at the corresponding time point. 3(D) The invasion ability of 4T1-wt or 4T1-ApoA1 were detected by a Transwell chamber experiment. The results were obtained from three independent repeated experiments.

FIGS. 4(A)-4(D) show anti-tumor effect of the recombinant oncolytic adenovirus AD5 ApoA1 in vivo (4T1 breast cancer solid tumor model). The anti-tumor effect of AD5 ApoA1 on a 4T1 subcutaneous tumor model of breast cancer was evaluated, and the experimental scheme was shown in FIG. 4(A). 4(B) After Balb/c mice were subcutaneously inoculated at the right side with $1\times10^5$ 4 T1 mouse breast cancer cells, and $2.5\times10^8$ pfu (plaque forming unit) AD5 CON or AD5 ApoA1 was injected intratumorally, the tumor size was monitored in real time. 4(C) After the mice were sacrificed on Day 10 after treatment, the tumors were separated to measure size and weight 4(D) The body weight of the mice after treatment. The data was obtained from three independent repeated experiments. *, $p<0.05$.

FIGS. 5(A)-5(D) show anti-tumor effect of the recombinant oncolytic adenovirus AD5 ApoA1 in vivo (4T1 carcinoma in situ model). The anti-tumor effect of AD5 ApoA1 on the 4T1 carcinoma in situ model was evaluated, and the experimental scheme was shown in FIG. 5(A). Balb/c mice were inoculated with $1\times10^5$ 4 T1 cells in the right mammary gland, and $2.5\times10^8$ pfu AD5 CON or AD5 ApoA1 were injected intratumorally. The tumor sizes were monitored in real time. 5(B) A mouse breast cancer in situ metastasis model was successfully established, and untreated tumor-bearing mice would have metastases invading the peritoneum and lung metastases. 5(C) The size of tumors in situ in the mice. 5(D) The survival of the mice. The data was obtained from three independent repeated experiments. *, $p<0.05$; **, $p<0.01$.

FIGS. 8(A)-8(D) show in vivo anti-tumor effects of the recombinant oncolytic adenovirus AD5 ApoA1 of an embodiment of the present invention (H22 subcutaneous tumor model). The anti-tumor effect of AD5 ApoA1 on the H22 subcutaneous tumor model was evaluated, and the experimental scheme was shown in FIG. 8(A). 8(B) After Balb/c mice were subcutaneously inoculated with $1\times10^6$ H22 mouse liver cancer cells and the mice developed tumors, $2.5\times10^8$ pfu AD5 CON or AD5 ApoA1 was injected intratumorally, and the tumor sizes were monitored in real time. 8(C) The tumor growth in each mouse. 8(D) The survival of the mice. **, $p<0.01$.

FIG. 11 shows that the adenovirus up-regulated the expression level of an ApoA1 receptor molecule Abca1 in tumor tissues. Balb/c mice were inoculated with 4T1 tumor cells. After tumor formation, $2.5\times10^8$ pfu AD5 CON or AD5 ApoA1 virus was injected intratumorally. After 48 h, tumor tissue RNA was extracted for RNAseq detection. The figure showed the relative expression level, which was calculated by setting the expression level of PBS group as 1, and the ratio of the expression levels of other groups to that of the PBS group as the relative expression level of those group, respectively.

FIGS. 12(A)-12(B) shows that the recombinant replicative oncolytic adenovirus AD5 ApoA1 of an embodiment of the present invention inhibited activation of stat1, stat3 and NFkB signal pathways and secretion of TNF-alpha, IL-6 and IL-1beta. (A) Human mononuclear macrophages THP-1 or human liver cancer cells HCC-LM3 were infected with AD5 ApoA1 or AD5 CON at an MOI of 5 for 24 h, or after TNF-a was added for stimulation for 30 min, the phosphorylation levels of stat1, stat3 and IkBa in the cells were measured. (B) The expression levels of TNF-alpha, IL-6 and IL-1 beta in the supernatants of HCC-LM3 were quantified by qPCR. *, $p<0.05$, **, $p<0.01$, compared with an AD5 CON group; and #$p<0.05$, compared with a PBS group. The data was obtained from the results of three independent repeated experiments.

ApoA1 or AD5 CON at an MOI of 5 for 24 h. After IL-6 was added for stimulation for 30 min, the expression levels of IDO1 in the cells were measured. The data was obtained from the results of three independent repeated experiments.

Figure 14:
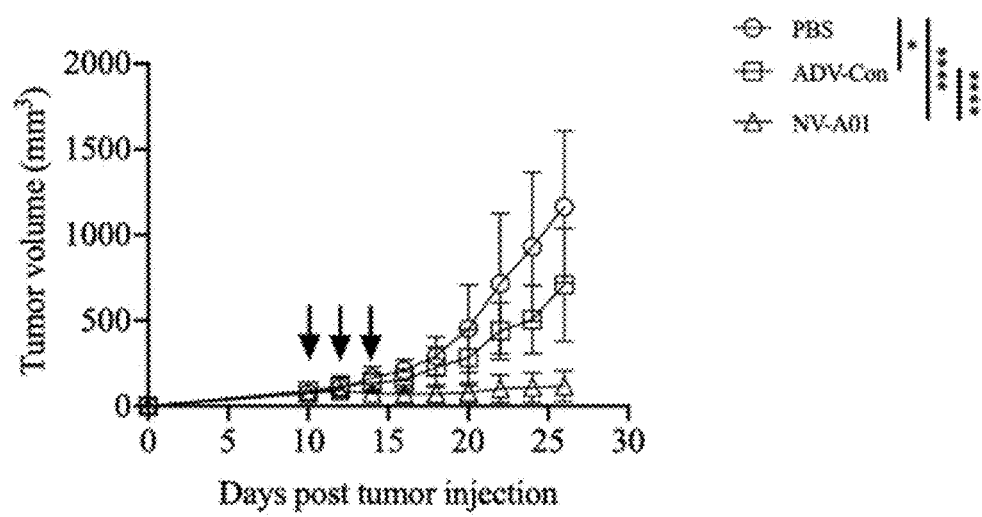

FIG. 14 shows in vivo anti-tumor effect of the recombinant oncolytic adenovirus AD5 ApoA1 of an embodiment of the current disclosure on a subcutaneous GL261 glioma model. The anti-tumor effect of AD5 ApoA1 on the subcutaneous GL261 glioma model was evaluated, and the tumor sizes measured were shown in FIG. 14 after C57Bl6 mice were subcutaneously inoculated with $5 \times 10^6$ GL261 glioma cells and the mice developed tumors to 100 mm$^3$, $3 \times 10^8$ pfu AD5 CON (ADV-Con) or AD5 ApoA1 (NV-A01) was injected intratumorally on days 1, 3, and 5, respectively. The tumor sizes were monitored in real time. The data was obtained from the results of three independent repeated experiments. *, $p<0.05$, ****, $p<0.0001$.

Figure 15:
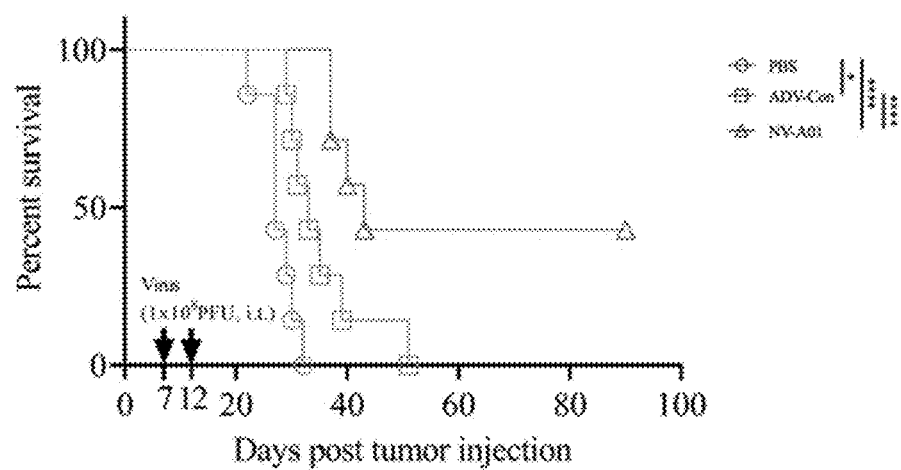

FIG. 15 shows in vivo anti-tumor effect of the recombinant oncolytic adenovirus AD5 ApoA1 of an embodiment of the current disclosure on an orthotopic GL261 glioma model. The anti-tumor effect of AD5 ApoA1 on the orthotopic GL261 glioma model was evaluated and the survival rate was shown in FIG. 15 after C57Bl6 mice were intracranially inoculated with $2 \times 10^6$ GL261 glioma cells and the mice developed tumors, $1 \times 10^8$ pfu AD5 CON (ADV-Con) or AD5 ApoA1 (NV-A01) was injected intratumorally. The survival rate was monitored in real time. The data was obtained from the results of three independent repeated experiments. *, $p<0.05$, ****, $p<0.0001$.

Figure 16:
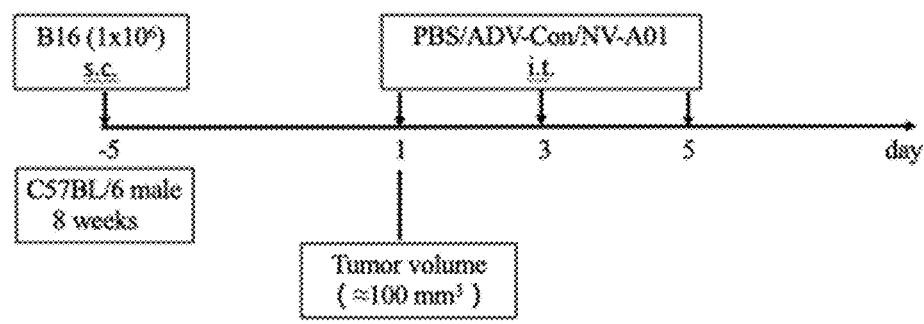
Figure 16:
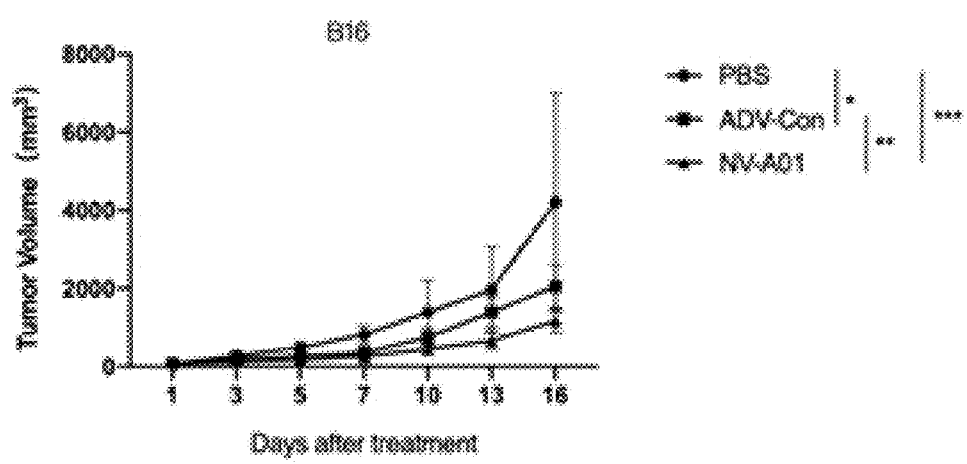

FIGS. 16(A)-16(B) shows in vivo anti-tumor effect of the recombinant oncolytic adenovirus AD5 ApoA1 of an embodiment of the current disclosure on a B16 melanoma model. The anti-tumor effect of AD5 ApoA1 on the B16 melanoma model was evaluated, and the experimental scheme was shown in 16(A). C57B16 mice were subcutaneously inoculated with $1 \times 10^6$ B16 cells. PBS (100 µL), AD5 CON (ADV-Con) ($5 \times 10^8$ pfu/mouse, 100 µL), and AD5 ApoA1 (NV-A01) ($5 \times 10^8$ pfu/mouse, 100 µL) were injected intratumorally. The tumor sizes were monitored in real time. 16(B) The tumor growth in situ of the mice. The data was obtained from three independent repeated experiments. *, $p<0.05$; , $p<0.01$, *, $p<0.001$.

Figure 17:
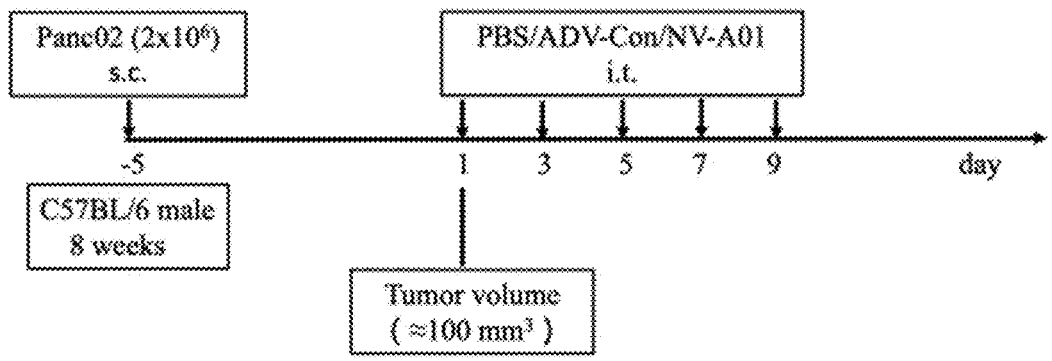
Figure 17:
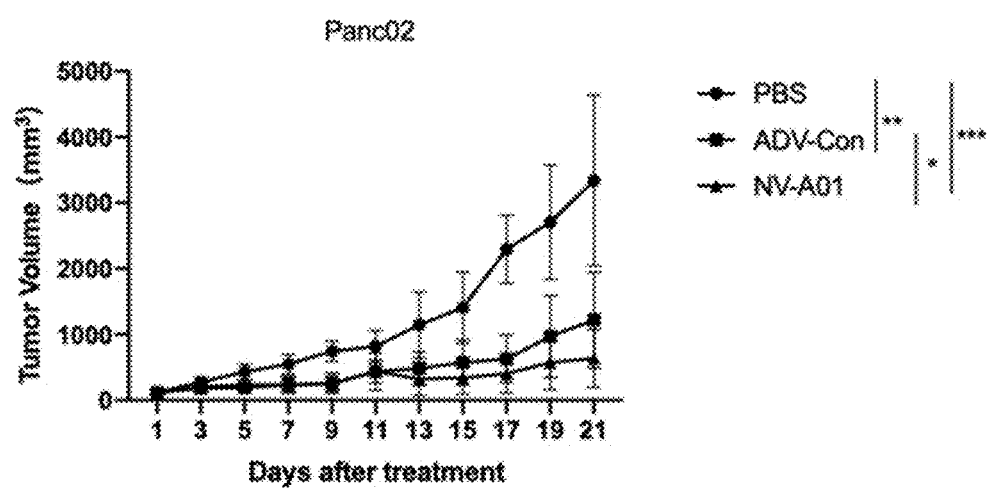

FIGS. 17(A)-17(B) shows in vivo anti-tumor effect of the recombinant oncolytic adenovirus AD5 ApoA1 of an embodiment of the current disclosure on a Panc02 pancreatic carcinoma model. The anti-tumor effect of AD5 ApoA1 on the Panc02 pancreatic carcinoma model was evaluated, and the experimental scheme was shown in 17(A). C57Bl/6 mice were subcutaneously inoculated with $2 \times 10^6$ Panc02 cells. PBS (100 µL), AD5 CON (ADV-Con) ($5 \times 10^8$ pfu/mouse, 100 µL) and AD5 ApoA1 (NV-A01) ($5 \times 10^8$ pfu/mouse, 100 µL) were injected intratumorally. The tumor sizes were monitored in real time. 17(B) The tumor growth in situ of the mice. The data was obtained from three independent repeated experiments. *, $p<0.05$; , $p<0.01$, *, $p<0.001$.

DETAILED DESCRIPTION

Aspects of the present invention are further explained and illustrated below with reference to specific embodiments. However, it is to be understood that the embodiments provided are merely for exemplary descriptions and should not be construed to limit the present invention in any manner.

The experimental equipments, materials and reagents involved in certain embodiments of the present invention are as follows:

(1) Cell Lines Used in Experiments

Human embryonic renal cell line 293T, human liver cancer cell line HCC-LM3 and SMMC-7721, human renal clear cell cancer cell line 786-0, human liver cancer cell line HuH-7 and HepG2, human bladder cancer cell line T24, human lung cancer cell line H1299, mouse liver cancer cell line H22, and mouse breast cancer cell line 4T1, cultured in a high-glucose DMEM medium supplemented with 10% fetal bovine serum, 100 U/I penicillin and 1 mg/ml streptomycin in an incubator containing 5% $CO_2$ at 37° C.

(2) Instruments Used in Experiments

Biological safety cabinet (SteriGARD®III advance, Class II Biological Safety Cabinet, The Baker Company), $CO_2$ incubator (FORMA SERIES II WATER JACKET $CO_2$ incubator, Thermo), refrigerated centrifuge (HERAEUS MEGAFUGE 1.0R, Thermo), vertical electrophoresis cell (BIO-RAD), electrophoresis apparatus (BIO-RAD), semi-dry electrophoretic transfer cell (BIO-RAD), Western Blot Exposure System (Alpha Innotech), PCR instrument (PCR Thermal Cycler Dice, TaKaRa), real-time quantitative PCR instrument and analysis software (AB1384, Sequence Detection Software, Version 1.3.1), microplate reader (VERSA max microplate reader), complete pipette set (eppendorf and RAININ), cell counter (Countstar Automated cell counter, Inno-Alliance Biotech Inc., Wilmington, USA), flow cytometer (FACSCalibur, Becton, Dickinson and Company, USA), FlowJo software (Version 7.6.5, Tree Star Inc, Ashland, Oreg.), microplate oscillator (QiLinBeiEr), nucleic acid purity concentration detector (Biophotometer plus, eppendorf), and digital display constant temperature water bath (Guohua Electric Appliance).

(3) Main Reagents and Consumables Used in Experiments

Primers, synthesized by Gen Script. DMEM high-glucose medium, diantibodies and serum required for tumor cell culture, purchased from Invitrogen (Shanghai). Quantitative RT-PCR reagents, Faststart Universal SYBR Green Master (Roche, 04913914001). Reagents and consumables required for Western Blot: protease inhibitor (Roche, 11873580001), cell lysate (Beyotime: P0013), PVDF membrane (Roche, 03010040001), WB Immobilon ECL solution (Millipore, WBKLS0500), primary antibody diluent (Beyotime, P0023A), HRP-tagged secondary antibody (Multisciences, GAR007 and GAM007, 1:5000 diluted), and the remaining reagents, domestically produced and analytical grade, purchased from the School of Chemistry and Chemical Engineering, Nanjing University. Trypan Blue (Beyotime, C0011). Opti-MEM, purchased from Invitrogen (Shanghai). Western Blot antibody: anti-His (GenScript, MB001, 1:5000 diluted).

Example 1: Plasmid Construction, Rescue and Amplification of AD5 ApoA1 Virus (1) Construction of a Full-Length AD5 ApoA1 Plasmid: A constructed shuttle vector AD5-pShuttle-ApoA1 was linearized with PmeI and transformed into competent pAdEasy-BJ5183. Screening was conducted using an LB plate containing 50 µg/mlkanamycin, and positive clones were selected for culture and identification. Clone plasmids identified as correct were retransformed into DH5a competent cells for secondary screening and identification. Once confirmed to be the correct clone plasmids, plasmid mass extraction was conducted to obtain the full-length AD5 ApoA1 plasmid.

(2) AD5 ApoA1 Virus Rescue:

The full-length AD5 ApoA1 plasmid was linearized with PacI, transfected into 293T cells (1 μg/well) in a 6-well plate after purification, and cultured in 5% $CO_2$ at 37° C. After 2 days, the cells were digested and transferred to a 10 cm plate, the medium on which was changed every 2-3 days until 80% of the cells showed a cytopathic effect. The cells were blown down using 10 ml of medium, collected into a 15 ml centrifuge tube, frozen and thawed twice, and centrifuged at 3000 rpm/min for 15 min. The virus supernatant was collected and stored at −80° C. as a virus seed.

(3) Virus Amplification:

50 μl of the virus seed solution was added to 60% 293T cells in a 10 cm plate. The cells were cultured in 5% $CO_2$ at 37° C. until the cell density reached to 90% or above. Subculturing was conducted according to a ratio of 1:3 until 80% of the cells showed a cytopathic effect, to obtain about 10 plate of cells. The viruses were collected as described supra, and purified by cesium chloride density gradient centrifugation. The titer was determined by a $TCID_{50}$ method.

Example 2: Titer Determination of AD5 ApoA1 Virus (1) 293T cells were inoculated in a 96-well plate with approximately $1\times10^3$ cells per well, and the titer was determined after cell adhesion.

(2) Gradient dilution of virus: EP tubes were prepared, and 1170 μl of DMEM containing fetal bovine serum was added to each EP tube. 130 μl of a virus solution was added to a first EP tube, mixed well, and marked as 10-1; 50 μl of the virus solution was pipetted from the first EP tube into a second EP tube, mixed well, and marked as 10-2; and so on, until the dilution reached the desired gradient.

(3) each well was added 100 μl of a virus diluent with a corresponding gradient, 10 wells for each gradient, and the virus diluents were cultured overnight at 37° C.

(4) After 5 days, the 96-well plate was placed under a microscope to observe GFP, and the number of wells with GFP at each gradient was recorded for calculation of virus titer.

(5) The virus titer $TCID_{50}$ was calculated by the following formula:

$$Log_{10}(TCID_{50})=L+d(s-0.5)+log_{10}(1/v)$$

L=$Log_{10}$ Highest degree of dilution, e.g., if the highest degree of dilution is 10 times dilution, L=1
V=Initial volume of cell culture medium per well (ml/well)
d=$Log_{10}$ Degree of dilution, e.g., if 10 times dilution, d=1
s=Sum of GFP ratios at all gradients Example 3: Function Evaluation of AD5 ApoA1 Virus (1) Expression and Secretion Functions of ApoA1:

72 h after tumor cells were infected with the AD5 ApoA1 virus, cells and supernatants were collected, and the expression and secretion functions of ApoA1 were determined by dot Blot.

(2) Viral Replicative Capacity:

Tumor cells were infected with AD5 ApoA1 and AD5 CON viruses at the same MOI. Cells were collected at different time points. Freezing, thawing and centrifugation were repeated to obtain virus suspensions of the same amount. The virus titer was determined by 293T cells. Changes in the virus replicative capacity were analyzed.

(3) Oncolytic Function:

Tumor cells were infected with the AD5 ApoA1 and AD5 CON viruses at an MOI of 1 to 100, and the cell activity was detected by MTT 72 h later to evaluate the anti-tumor effect of AD5 ApoA1.

Example 4: Construction of Stable Transfected Cell Line of 4T1-ApoA1

(1) 18-24 h before lentiviral transfection, adherent cells were spread in a 24-well plate ($1\times10^5$/well), depending on the cell sizes, generally the cells grew to 40-60% before transfection. The number of cells was $2\times10^5$/well during lentivirus transfection.

(2) 6 μg/ml polybrene was added, and ApoA1 having CMV as a promoter was added at the same time to overexpress the lentivirus. Culturing continued for 48 h.

(3) 2 μg/ml puromycin was added to screen cells. The medium was changed every day until the cells in negative control wells died completely.

Example 5: 4T1 Clone Formation and Invasion Experiment (1) Cell Clone Acquisition
1) Cell density was adjusted to 100 cells/30 μl.
2) An appropriate amount of sterile PBS was added to the bottom of a 10 cm culture plate, and 30 μl of cell suspension was dropped on a lid.
3) After cultured for 2-3 days, the clustering state of the cells was observed under a microscope.
4) After cell clones were formed, the cell clones were inoculated in a 96-well plate coated with type I collagen, and morphology of the cell clones was monitored in real time.

(2) Transwell Experiment
1) Matrix was diluted 30 times, and 40 μl was added to each chamber, and solidified for use (plated the day before the experiment).
2) Cells were digested and centrifuged, and counted after changed to a serum-free medium or (2% serum).
3) 50,000-100,000 cells/200 μl were added to each chamber, and 700 μl of complete medium was added to a lower chamber.
4) The cells were immobilized and dyed about 24 h later, Matrigel was wiped off with cotton balls, and pictures were taken under a microscope.

Example 6: Study on Anti-Tumor Effect and Mechanism of AD5 ApoA1 In Vivo 6-8 week-old Balb/c mice were used to establish subcutaneous tumor models in the right armpit or subcutaneously, tumor size was measured after 4-6 days to reach 200 $mm^3$. The mice were randomly divided into 3 groups, namely: a blank control group, an AD5 CON virus therapy control group, and an AD5 ApoA1 virus therapy group. The corresponding virus was intratumorally injected to the groups accordingly, each with a virus injection amount of $2.5\times10^8$ pfu. Tumor volume and body weight were tracked and measured. After the mice died naturally, survival time of the mice was recorded.

Example 7: Extraction and Concentration Determination of Total Cell Protein

Taking a six-well plate as an example, a cell culture supernatant was removed, the cells were washed twice with PBS, the PBS was removed, 200 µl of pancreatin was added per well, the cells were digested and pipetted, and then collected into an EP tube and centrifuged at 1500 rpm for 5 min.

The supernatant was removed, PBS was added to resuspend the cells, and the cell resuspension was centrifuged at 1500 rpm for 5 min.

The PBS was removed. A corresponding cell lysate containing a protease inhibitor was added to each well according to the amount of cells, vortexed for 30 s, and placed on ice for 10 min, and the operations were repeated three times. Centrifugation was conducted at 12000 g for 15 min at 4° C. The supernatant was collected in another clean EP tube.

Determination of protein concentration: Protein concentration was determined according to the manual of a BCA protein assay kit. 2 µl of a protein sample was added to a 96-well plate, 18 µl of PBS was added to dilute the sample, and finally 200 µl of an assay working solution (containing a reagent A and a reagent B in a ratio of 50:1) was added. The plate was placed in an oven at 60° C. After 30 min, absorbance at 562 nm was measured with a microplate reader, and the concentration of the protein sample was calculated according to a standard curve.

A 5×loading buffer of ¼ volume of a protein lysate was added to each tube and mixed well, and the tube was placed in a metal bath at 100° C. for 5 min. After cooling, the resulting solution was stored at −20° C. for use.

Example 8: Western Blot Experiment

Gel preparation and electrophoresis: SDS-PAGE separation gels and stacking gels of different concentrations were prepared as desired. The loading volume of each sample was adjusted to 30 µg based on the calculated protein quantification. Electrophoresis conditions: Stacking gel: 80 V, 30 min; separation gel: 120 V, about 80 min, provided that strips were separated and did not run out.

Membrane transfer: Filter paper and a PVDF membrane were prepared, the PVDF membrane was soaked in methanol first, and then soaked with the filter paper in a transfer buffer to be ready for use. The gel was carefully removed from a glass plate and soaked in the transfer buffer solution, and a negative electrode, the filter paper, the PVDF membrane, the gel, the filter paper and a positive electrode were placed in a sequential order like a sandwich, and bubbles were extruded. The membrane was transferred at constant current 110 mA for 60-70 min as desired based on the band sizes.

Blocking: After the membrane transfer, the PVDF membrane was immediately taken out and put in 5% skimmed milk powder and blocked at room temperature for 1 h.

Primary antibody incubation: Incubated with the primary antibody overnight at 4° C.

Secondary antibody incubation: The bands were washed with a washing buffer for three times, 10 min each time; and then the strips were incubated with the corresponding HPR-tagged secondary antibody for 1 h at room temperature.

Exposure: The strips were washed with a washing buffer for three times, 10 min each time. The strips were exposed with a chemiluminescent solution on a WB exposure instrument, and the strip images were acquired.

Example 9: Counting with Trypan Blue

Taking a six-well plate as an example, cell supernatant was removed, the cells were washed with PBS twice, the PBS was removed, 200 µl of pancreatin was added per well for digestion, and the cells were pipetted gently, collected into a clean EP tube and centrifuged at 1500 rpm for 5 min. The supernatant was removed, PBS was added to resuspend the cells, and the cell resuspension was centrifuged at 1500 rpm for 5 min. PBS was removed, a certain amount of PBS was added according to the number of cells to be resuspended, 10 µl of the cell resuspension was taken out, 10 µl of a 0.2% trypan blue solution was added and mixed, 20 µl of the mixture was taken in a cell counting plate, and the cells were counted with a cell counter.

Example 10: Real-Time Quantitative PCR

A 10 µl system of real-time quantitative PCR included: 2.6 µl PCR water, 0.2 µl forward and reverse primers respectively, 2 µl template and 5 µl of SYBR Green fluorescent dye. After mixing with a sample, the sample was amplified on an ABI 384 PCR machine.

Example 11: Glioma Models (1). Subcutaneous GL261 Glioma Models 8-week-old male C57Bl6 mice were subcutaneously inoculated with $5\times10^6$ GL261 glioma cells. After tumor volume reached about 100 $mm^3$, the mice received intratumoral injection of oncolytic virus AD5 ApoA1 ($3\times10^8$ pfu/mouse) on Day 1, 3, and 5, respectively. Tumor volume was monitored every other day. Mice received intratumoral injection of either PBS or AD5 CON virus were used as controls.

(2). Orthotopic GL261 Glioma Models 8-week-old male C57BL/6 mice were intracranially inoculated with $2\times10^6$ GL261 glioma cells. On Day 7 and 12 after tumor inoculation, the mice received intratumoral injection of oncolytic virus AD5 ApoA1 ($1\times10^8$ pfu/mouse). Survival was monitored every other day. The mice intratumorally inoculated with either PBS or AD5 CON virus were used as controls.

Example 12: B16 Melanoma Models 8-week-old male C57BL/6 mice were subcutaneously inoculated with B16 melanoma cells ($1\times10^6$ cells/mouse). The mice were randomly divided into 3 groups on Day 5 when the tumor size reached 100 $mm^3$, followed by intratumoral injection of PBS (100 µL), AD5 CON ($5\times10^8$ pfu/mouse, 100 µL), and AD5 ApoA1 ($5\times10^8$ pfu/mouse, 100 µL), respectively. Viruses were injected for 3 times each mouse every other day at a dose of $5\times10^8$ pfu each injection. Tumor growth was monitored every other day. The mice intratumorally injected with either PBS or AD5 CON virus were used as controls.

Example 13: Panc02 Pancreatic Carcinoma Models 8-week-old male C57BL/6 mice were subcutaneously inoculated with Panc02 pancreatic carcinoma cells ($2\times10^6$ cells/mouse). The mice were randomly divided into 3 groups on Day 5 when the tumor size reached 100 $mm^3$, followed by intratumoral injection of PBS (100 µL), AD5 CON (5×10$^8$ pfu/mouse, 100 µL), and AD5 ApoA1 (5×10$^8$ pfu/mouse, 100 µL), respectively. Viruses were injected for 5 times each mouse every other day at a dose of 5×10$^8$ pfu each injection. Tumor growth was monitored every other day. The mice intratumorally injected with either PBS or AD5 CON virus were used as controls.

RESULTS AND CONCLUSIONS

Figure 1A:
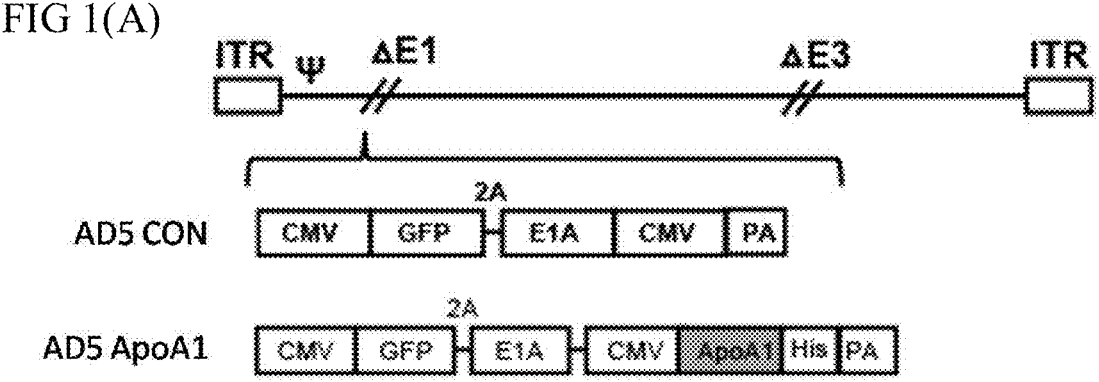
FIG. 1(A) shows a schematic diagram of a gene structure for construction of a recombinant oncolytic adenovirus AD5 ApoA1 expressing a soluble ApoA1 of an embodiment of the present invention.
Figure 1B:
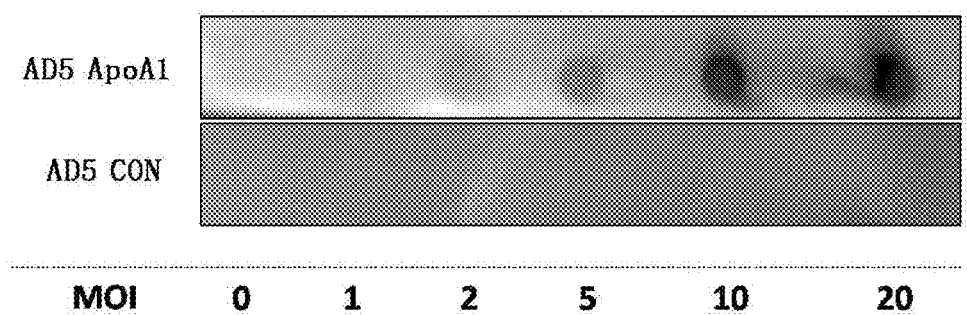
FIG. 1(B) shows that Hepa1-6 mouse liver cancer cells were respectively infected with AD5 CON and AD5 ApoA1 at various multiplicities of infection (MOI) in 72 h, supernatants of the infected cells were collected, and secretion of fusion proteins ApoA1 was determined by dot blot. The data was obtained from three independent repeated experiments. GFP represents green fluorescent proteins; E1A represents a virus early region 1 replication element (early region 1); ApoA1 represents free fusion proteins ApoA1; and His represents a histidine tag.
Figure 6A:
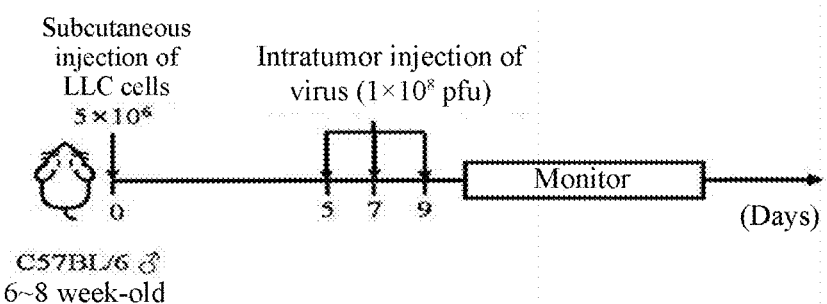
FIGS. 6(A)-6(C) show in vivo anti-tumor effect of the recombinant oncolytic adenovirus AD5 ApoA1 of an embodiment of the present invention (mouse lung cancer LLC subcutaneous tumor model). The anti-tumor effect of AD5 ApoA1 on the LLC subcutaneous tumor model was evaluated, and the experimental scheme was shown in FIG. 6(A). 6(B) C57/BL6 mice were subcutaneously inoculated with $5\times10^6$ LLC mouse lung cancer cells and the mice developed tumors, $1\times10^8$ pfu AD5 CON or AD5 ApoA1 was injected intratumorally, and the tumor sizes were monitored in real time. 6(C) The body weight of the mice. *, $p<0.05$.
Figure 6B:
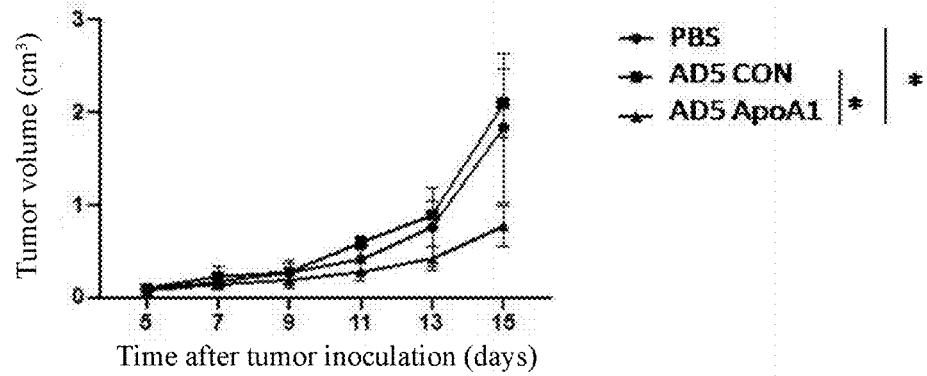
Figure 6C:
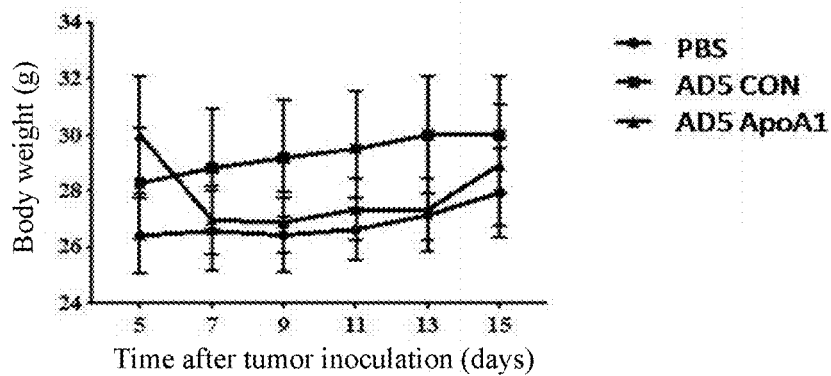

FIGS. 1(A)-1(B) show that the replicative oncolytic adenovirus AD5 ApoA1 was successfully constructed. The ApoA1 protein designed had both its own signal peptide and histidine tag. Experiments showed that the designed signal peptide of ApoA1 allowed extracellular secretion of ApoA1.

FIGS. 2(A)-2(E) show that compared with the control virus, the constructed replicative oncolytic adenovirus AD5 ApoA1 had a stronger replicative capacity in human liver cancer cell line HCC-LM3 and SMMC-7721, human renal clear cell carcinoma cell line 786-0, human liver cancer cell line HuH-7 and HepG2, human bladder cancer cell line T24, and human lung cancer cell line H1299; and showed a stronger oncolytic ability in Huh-7 and T24. It was also found from in vivo experiments that the viral load of the replicative AD5 ApoA1 in tumors was significantly higher than that of AD5 CON 2 days after the virus injection of the same dose. It indicates that the expression of ApoA1 could promote replication and oncolysis of the adenovirus.

FIGS. 3(A)-3(D) show that a scratch gap of breast cancer cells with high expression of the apolipoprotein ApoA1 was larger than that of the control group. The range and distance of invasion and metastasis of breast cancer cells expressing ApoA1 in Matrigel were significantly reduced compared with the control group. A chamber invasion experiment found that the number of breast cancer cells expressing ApoA1 was significantly less than the number of permeable cells in the control group. It indicates that the ApoA1 protein could inhibit metastasis and invasion of breast cancer cells.

FIGS. 4(A)-4(D) show that the 4T1 subcutaneous tumor volume of mice injected with the AD5 ApoA1 adenovirus was smaller than the tumor volume of the control virus and PBS treatment groups. It indicates that in the mouse models, the replicative oncolytic adenovirus AD5 ApoA1 significantly inhibited the growth of breast cancer.

FIGS. 5(A)-5(D) show that compared with the control virus and PBS treatment groups, the 4T1 breast cancer in situ tumor volume of mice injected with the AD5 ApoA1 adenovirus was smaller; tumor invasion in the abdominal cavity and lung metastases significantly decreased; and the survival rate of mice was higher. It indicates that the replicative AD5 ApoA1 significantly inhibited the invasion, metastasis and distant metastasis of breast cancer in situ, and significantly prolonged the survival time of the mice with breast cancer.

FIGS. 6(A)-6(D) show that the lung cancer LLC subcutaneous tumor volume of mice injected with the AD5 ApoA1 adenovirus was smaller than that of the control virus and the PBS treatment groups, indicating that the AD5 ApoA1 adenovirus significantly inhibited the growth of mouse lung cancer in mice.

Figure 7A:
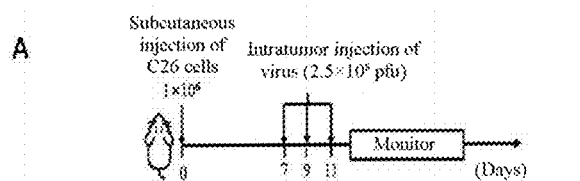
FIGS. 7(A)-7(c) show in vivo anti-tumor effect of the recombinant oncolytic adenovirus AD5 ApoA1 of an embodiment of the present invention (C26 subcutaneous tumor model of colon cancer cells that can cause cachexia). The anti-tumor effect of AD5 ApoA1 on the C26 subcutaneous tumor model was evaluated, and the experimental scheme was shown in FIG. 7(A). 7(B) Balb/c mice were subcutaneously inoculated with $1\times10^6$ C26 mouse colon cancer cells and after the mice developed tumors, $2.5\times10^8$ pfu AD5 CON or AD5 ApoA1 was injected intratumorally, and the tumor sizes were monitored in real time. 7(C) The body weight of the mice (the degree of weight loss reflected the level of progression of cachexia symptoms). *, $p<0.05$.
Figure 7B:
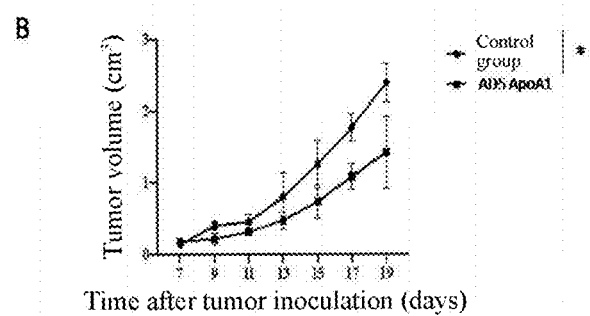
Figure 7C:
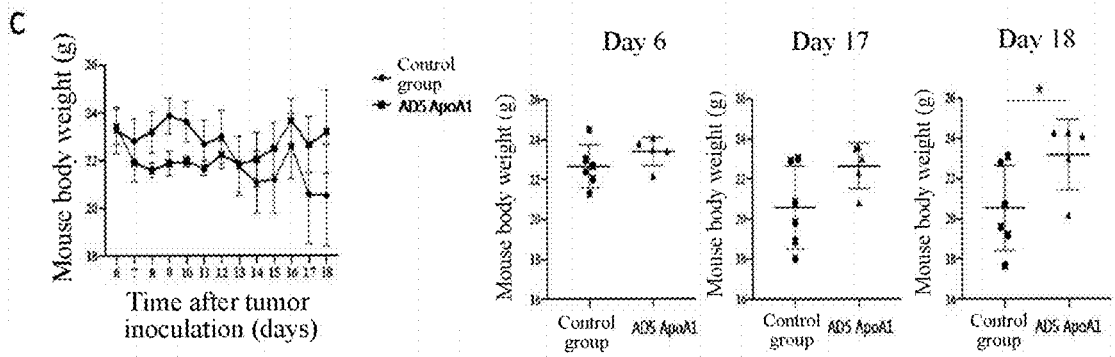

FIGS. 7(A)-7(C) show that the colon cancer C26 subcutaneous tumor volume in mice injected with the replicative AD5 ApoA1 was smaller than that of the control treatment group, and the replicative AD5 ApoA1 had a significant alleviation effect on cachexia symptoms (rapid weight loss) caused by C26 tumors. It indicates that the AD5 ApoA1 adenovirus significantly inhibited the growth of mouse colon cancer C26 subcutaneous tumors in mice, and significantly delayed the progression of cachexia.

FIGS. 8(A)-8(D) show that compared with the control virus and PBS treatment groups, the H22 liver cancer subcutaneous tumor volume in mice injected with the AD5 ApoA1 adenovirus was smaller, and the survival rate of the mice was higher. It indicates that the AD5 ApoA1 adenovirus significantly inhibited the growth of liver cancer in mice and prolonged the survival of mice.

Figure 9A:
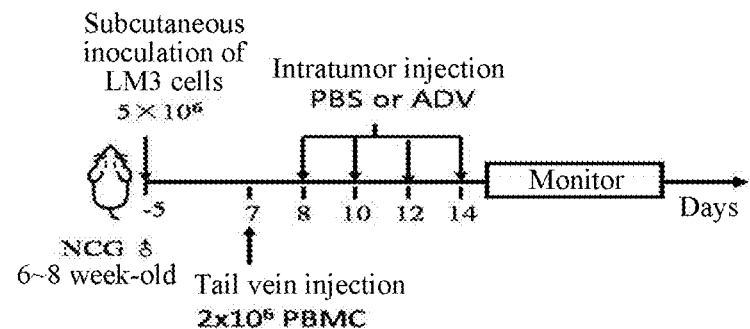
FIGS. 9(A)-9(B) show anti-tumor studies of the recombinant oncolytic adenovirus AD5 ApoA1 of an embodiment of the present invention in a humanized mouse model (LM3 subcutaneous tumor). 9(A) The experimental scheme. NCG (NOD-Prkdc$^{scid}$ Il2rg$^{null}$) mice were subcutaneously inoculated with $5\times10^6$ LM3 human liver cancer cells, and $2\times10^6$ human peripheral blood mononuclear cells (PBMC) were injected through the tail vein after tumors appeared in the mice. Then, $2\times10^8$ pfu AD5 CON or AD5 ApoA1 was injected intratumorally. 9(B) Measurement of the tumor sizes. The data was obtained from the results of three independent repeated experiments. *, $p<0.05$.
Figure 9B:
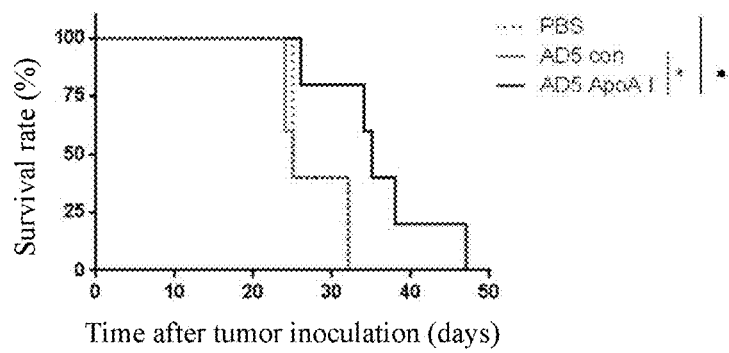

FIGS. 9(A)-9(B) show that the replicative AD5 ApoA1 significantly prolonged the survival period of mice with humanized liver cancer.

Figure 10A:
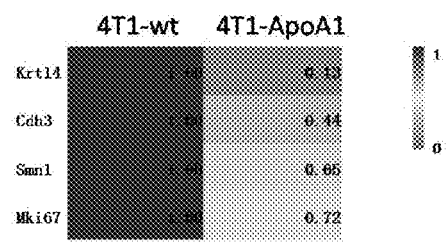
FIGS. 10(A)-10(B) show that ApoA1 proteins inhibited expression of breast cancer invasion-related proteins. 10(A) After 4T1-wt cells and 4T1-ApoA1 cells were cultured for 24 h, mRNA was extracted for conducting RNAseq. The relative expression levels were shown in the figures. The relative expression level was calculated by setting the expression level of 4T1-wt as 1 and the ratio of the expression level of 4T1-ApoA1 to that of 4T1-wt as the relative expression level of 4T1-ApoA1. 10(B) After the 4T1-wt cells and the 4T1-ApoA1 cells were cultured for 24 h, the expression level of Krt14 was quantified by qPCR. Krt14 represents keratin 14; Cdh3 represents cadherin 3; Smn1 represents Survival Of Motor Neuron 1, Telomeric; and Mki67 represents a cell proliferation tagged molecule ki-67. **, $p<0.01$.
Figure 10B:
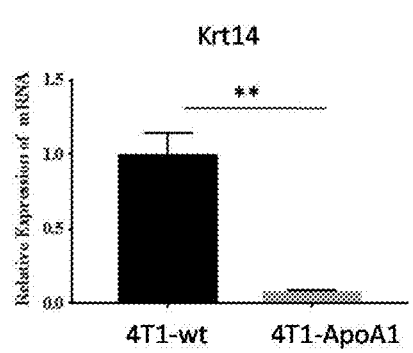

FIGS. 10(A)-10(B) show that the ApoA1 protein inhibited the expression of molecules related to the invasion and metastasis of breast cancer cells 4T1, especially keratin 14 (Krt14).

FIG. 11 shows that the replicative adenovirus up-regulated the expression of a specific receptor molecule Abca1 of ApoA1, thereby further enhanced the cholesterol transport ability of ApoA1.

FIGS. 12(A)-12(B) show that the replicative AD5 ApoA1 significantly inhibited activation of tumor-promoting inflammation pathways STAT3 and NFkB in macrophages and tumor cells, and reduced production of tumor-promoting inflammatory factors IL-6, NFkB and IL-1beta.

Figure 13:
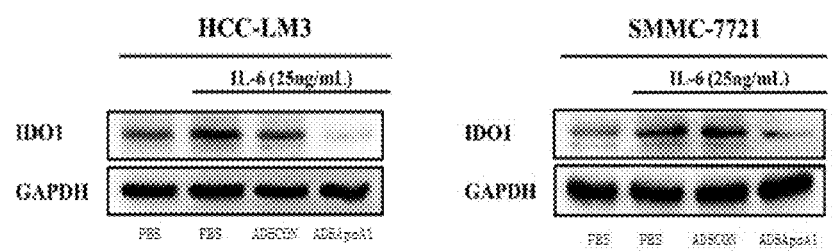
FIG. 13 shows that the recombinant replicative oncolytic adenovirus AD5 ApoA1 of an embodiment of the present invention inhibited expression of IDO1. Human liver cancer cells HCC-LM3 and SMMC-7721 were infected with AD5

FIG. 13 shows that the AD5 ApoA1 adenovirus inhibited expression of indoleamine 2,3 dioxygenase 1 (IDO1) of liver cancer cell line HCC-LM3 and SMMC-7721 in vitro, inhibited immune tolerance, and enhanced anti-tumor immunity.

FIG. 14 shows that the tumor volume of subcutaneous GL261 glioma of mice injected with AD5 ApoA1 was smaller than the tumor volume of mice injected with AD5 CON virus and PBS treatment groups. It indicates that in the subcutaneous GL261 glioma models, the replicative oncolytic adenovirus AD5 ApoA1 significantly inhibited the growth of subcutaneous GL261 glioma in vivo.

FIG. 15 shows that the survival rate of orthotopic GL261 glioma of mice injected with AD5 ApoA1 was higher than the survival rate of mice injected with AD5 CON virus and PBS treatment groups. It indicates that in the orthotopic GL261 glioma models, the replicative oncolytic adenovirus AD5 ApoA1 significantly prolonged the survival of mice.

FIGS. 16(A)-16(B) show that the tumor volume of B16 melanoma of mice injected with AD5 ApoA1 was smaller than the tumor volume of mice injected with AD5 CON virus and PBS treatment groups. It indicates that in the B16 melanoma models, the replicative oncolytic adenovirus AD5 ApoA1 significantly inhibited the growth of B16 melanoma in vivo.

FIGS. 17(A)-17(B) shows that the Panc02 pancreatic carcinoma tumor volume of mice injected with AD5 ApoA1 was smaller than the tumor volume of mice injected with AD5 CON virus and PBS treatment groups. It indicates that the oncolytic virus AD5 ApoA1 significantly inhibited the growth of Panc02 pancreatic carcinoma in vivo.

Accordingly, the present invention provides for the first time embodiments of the replicative oncolytic adenovirus AD5 ApoA1 capable of inhibiting tumor growth and blocking tumor invasion and metastasis. The virus not only had a stronger replicative and oncolytic capability in tumor cells than the Ad5 CON virus, but also can highly express the apolipoprotein ApoA1 that was secreted extracellularly, up-regulated the specific receptor ABCA1 of ApoA1 highly expressed by infected tumor cells, greatly enhanced the cholesterol transport effect of AD5 ApoA1, produced unexpected synergistic effects, and exerted multiple anti-tumor effects. AD5 ApoA1 inhibited invasion and metastasis of malignant tumor cells, blocked tumor-promoting inflammation pathways, inhibited a key enzyme IDO-1 which mediates tumor immune escape, and effectively restored the body's immune surveillance of tumors. Moreover, the recombinant replicative oncolytic adenovirus AD5 ApoA1 of certain embodiments of the present invention showed an unexpected effect against the progression of cachexia, effectively maintained the body weight of mice with colon cancer, and significantly extended the survival time. In general, the recombinant replicative oncolytic adenovirus AD5 ApoA1 of certain embodiments of the present invention simultaneously had multiple anti-tumor effects: inhibiting tumor invasion and metastasis, delaying a cachexia progress of malignant tumors, up-regulating the specific receptor ABCA1 of ApoA1 highly expressed by infected tumor cells for synergistic anti-tumor effects, inhibiting IDO-1 and tumor-promoting inflammation, and restoring anti-tumor immune surveillance. Certain embodiments of the virus integrated a variety of unique effects and mechanisms in tumor therapy simultaneously, which complemented each other and showed unexpected effects.

The foregoing describes basic principles, main features and advantages of the present invention. A person skilled in the art should understand that the present invention is not limited to the foregoing embodiments, and the foregoing embodiments and descriptions in the specification are only used to describe the principle of the present invention. The present invention may have various modifications and improvements without departing from the spirit or scope of the present invention. The scope of the claimed protection is defined by the appended claims, specification, and equivalents thereof.

What is claimed is:

1. A replicative oncolytic adenovirus vector comprising: an expression cassette comprising a first promoter, an E1A early activation replication element, an insulator sequence, a second promoter, and a target gene sequence, wherein:
   the expression cassette is inserted into an E1 region of an oncolytic adenovirus;
   the target gene sequence comprises a signal peptide recognition sequence or a degenerate sequence thereof, and an ApoA1 gene or a degenerate sequence thereof, wherein the ApoA1 gene has the nucleotide sequence of SEQ ID NO:1.

2. The replicative oncolytic adenovirus vector according to claim 1, wherein:
   (1) the first promoter is a constitutive promoter, a specific promoter, or an inducible promoter; and the second promoter is a constitutive promoter; and/or
   (2) the adenovirus is of subtype C.

3. The replicative oncolytic adenovirus vector according to claim 2, wherein the constitutive promoter is CMV, SV40, or EF1 a promoter.

4. The replicative oncolytic adenovirus vector according to claim 3, wherein the constitutive promoter is CMV having the nucleotide sequence of SEQ ID NO:2.

5. A replicative oncolytic adenovirus, comprising the replicative oncolytic adenovirus vector according to claim 1.

6. The replicative oncolytic adenovirus according to claim 5, wherein the protein expressed by the target gene has the amino acid sequence of SEQ ID NO:3.

7. The replicative oncolytic adenovirus according to claim 5, wherein the virus is obtained by recombination of the replicative oncolytic adenovirus vector according to claim 1 in 293T cells.

* * * * *

SEQUENCE LISTING

```
<160> NUMBER OF SEQ ID NOS: 3

<210> SEQ ID NO 1
<211> LENGTH: 819
<212> TYPE: DNA
<213> ORGANISM: Artificial Sequence
<220> FEATURE:
<223> OTHER INFORMATION: Synthetic

<400> SEQUENCE: 1
atgaaagctg cggtgctgac cttggccgtg ctcttcctga cggggagcca ggctcggcat      60
ttctggcagc aagatgaacc cccccagagc ccctgggatc gagtgaagga cctggccact     120
gtgtacgtgg atgtgctcaa agacagcggc agagactatg tgtcccagtt tgaaggctcc     180
gccttgggaa aacagctaaa cctaaagctc cttgacaact gggacagcgt gacctccacc     240
ttcagcaagc tgcgcgaaca gctcggccct gtgacccagg agttctggga taacctggaa     300
aaggagacag agggcctgag gcaggagatg agcaaggatc tggaggaggt gaaggccaag     360
gtgcagccct acctggacga cttccagaag aagtggcagg aggagatgga gctctaccgc     420
cagaaggtgg agccgctgcg cgcagagctc caagagggcg cgcgccagaa gctgcacgag     480
ctgcaagaga agctgagccc actgggcgag gagatgcgcg accgcgcgcg cgcccatgtg     540
gacgcgctgc gcacgcatct ggcccctac agcgacgagc tgcgcagcg cttggccgcg     600 cgccttgagg ctctcaagga gaacggcggc gccagactgg ccgagtacca cgccaaggcc     660
accgagcatc tgagcacgct cagcgagaag gccaagcccg cgctcgagga cctccgccaa     720
ggcctgctgc ccgtgctgga gagcttcaag gtcagcttcc tgagcgctct cgaggagtac     780
actaagaagc tcaacaccca gggggtgga ggctcttaa                             819

<210> SEQ ID NO 2
<211> LENGTH: 508
<212> TYPE: DNA
<213> ORGANISM: Artificial Sequence
<220> FEATURE:
<223> OTHER INFORMATION: Synthetic

<400> SEQUENCE: 2
cgttacataa cttacggtaa atggcccgcc tggctgaccg cccaacgacc cccgcccatt      60
gacgtcaata atgacgtatg ttcccatagt aacgccaata gggactttcc attgacgtca     120
atgggtggag tatttacggt aaactgccca cttggcagta catcaagtgt atcatatgcc     180
aagtacgccc cctattgacg tcaatgacgg taaatggccc gcctggcatt atgcccagta     240
```

```
catgacccta tgggactttc ctacttggca gtacatctac gtattagtca tcgctattac    300
catggtgatg cggttttggc agtacatcaa tgggcgtgga tagcggtttg actcacgggg    360
atttccaagt ctccacccca ttgacgtcaa tgggagtttg ttttggcacc aaaatcaacg    420
ggactttcca aaatgtcgta acaactccgc cccattgacg caaatgggcg gtaggcgtgt    480
acggtgggag gtctatataa gcagagct                                      508
```

```
<210> SEQ ID NO 3
<211> LENGTH: 272
<212> TYPE: PRT
<213> ORGANISM: Artificial Sequence
<220> FEATURE:
<223> OTHER INFORMATION: Synthetic

<400> SEQUENCE: 3

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln Gly Gly Gly Gly Ser
            260                 265                 270
```